(12) United States Patent
Konya et al.

(10) Patent No.: US 8,202,232 B2
(45) Date of Patent: Jun. 19, 2012

(54) LANCING SYSTEM

(75) Inventors: Ahmet Konya, Waldsee (DE); Klaus Schoettle, Willstatt (DE); Karl-Peter Ebert, Fraenkisch-Crumbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 163 days.

(21) Appl. No.: 12/394,076

(22) Filed: Feb. 27, 2009

(65) Prior Publication Data

US 2010/0049090 A1 Feb. 25, 2010

Related U.S. Application Data

(63) Continuation-in-part of application No. PCT/EP2008/006797, filed on Aug. 19, 2008.

(30) Foreign Application Priority Data

Aug. 28, 2007 (EP) .................................. 07016808

(51) Int. Cl.
*A61B 5/00* (2006.01)
(52) U.S. Cl. ....................................................... 600/583
(58) Field of Classification Search .................. 600/583, 600/584; 606/181, 182, 183
See application file for complete search history.

(56) References Cited

U.S. PATENT DOCUMENTS

| 4,218,421 | A | 8/1980 | Mack et al. |
| 4,687,157 | A * | 8/1987 | Schoettle et al. .......... 242/345.2 |
| 6,988,996 | B2 * | 1/2006 | Roe et al. ...................... 600/584 |

| 2002/0188224 | A1 | 12/2002 | Roe et al. |
| 2003/0199903 | A1 * | 10/2003 | Boecker et al. ............... 606/181 |
| 2003/0211619 | A1 | 11/2003 | Olson et al. |
| 2005/0245845 | A1 | 11/2005 | Roe et al. |

(Continued)

FOREIGN PATENT DOCUMENTS

DE 28 03 345 B1 6/1979

(Continued)

OTHER PUBLICATIONS

International Patent Application PCT/EP2008/006797 International Search Report mailed Jan. 23, 2009.

(Continued)

*Primary Examiner* — Max Hindenburg
*Assistant Examiner* — Charles Becker
(74) *Attorney, Agent, or Firm* — Woodard, Emhardt, Moriarty, McNett & Henry LLP

(57) ABSTRACT

The invention relates to a lancing system having a lancet carrier tape (3) supporting a plurality of lancets (4), a transport means (5, 11, 17) serving to move the lancet carrier tape (3) in a feed or transport direction along a transport path and to thereby move lancets (4) of the lancet carrier tape (3) one after the other to a puncturing position, and a lancing drive (6) for causing a lancet (4) that occupies a puncturing position to perform a puncturing movement. It is provided according to the invention that during a puncturing movement the lancing drive (6) moves a lancet (4), that has been brought to a puncturing position, in the puncturing direction together with a portion of the lancet carrier tape (3) on which that lancet (4) is supported and that once a lancet (4) has been moved to the puncturing position at least one element of the transport means (5, 11, 17), arranged behind the puncturing position in the transport direction, performs a movement before or during the puncturing movement of that lancet (4).

26 Claims, 8 Drawing Sheets

U.S. PATENT DOCUMENTS

| | | |
|---|---|---|
| 2005/0245954 A1 * | 11/2005 | Roe et al. ............ 606/181 |
| 2006/0240403 A1 | 10/2006 | List et al. |
| 2007/0038150 A1 * | 2/2007 | Calasso et al. ........ 600/583 |
| 2007/0173740 A1 * | 7/2007 | Chan et al. ........... 600/583 |
| 2008/0103415 A1 | 5/2008 | Roe et al. |

FOREIGN PATENT DOCUMENTS

| | | |
|---|---|---|
| DE | 10 2005 013 685 A1 | 9/2006 |
| EP | 1 790 288 A1 | 5/2007 |
| EP | 1 801 584 A1 | 6/2007 |
| WO | WO 2004/056269 A1 | 7/2004 |
| WO | WO 2005/104948 A1 | 11/2005 |
| WO | WO 2007/073912 a1 | 7/2007 |
| WO | WO 2007/147494 A2 | 12/2007 |

OTHER PUBLICATIONS

DE 28 03 345 B1 English Language Translation, Dated Jun. 13, 1969.
EP 1 790 288 Al English Language Abstract, Dated May 30, 2007.

* cited by examiner

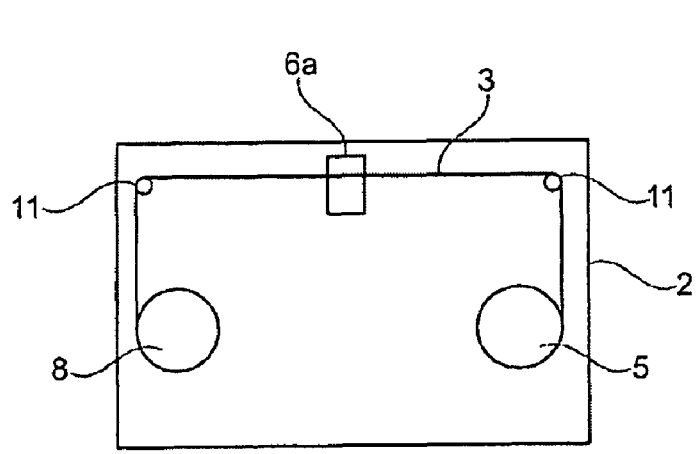
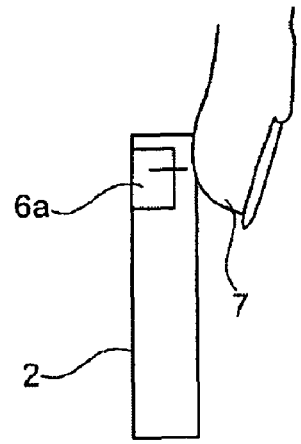
Fig. 5    Fig. 6
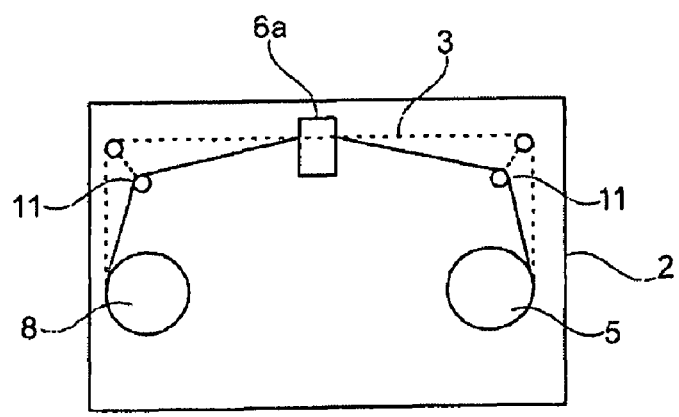
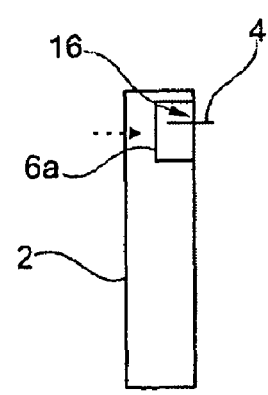
Fig. 7    Fig. 8

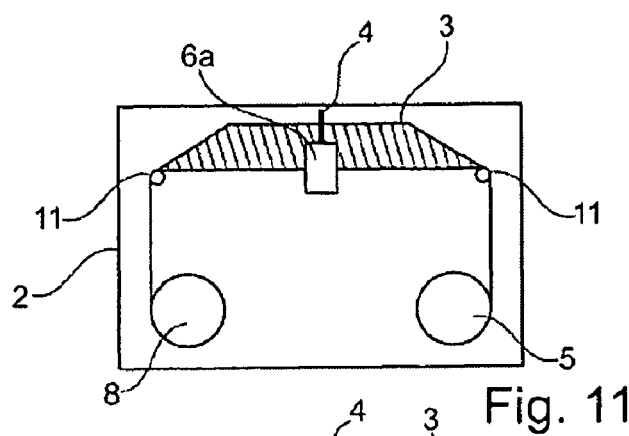 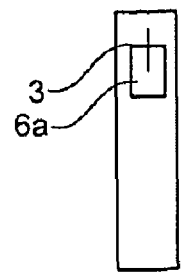
Fig. 11  Fig. 12
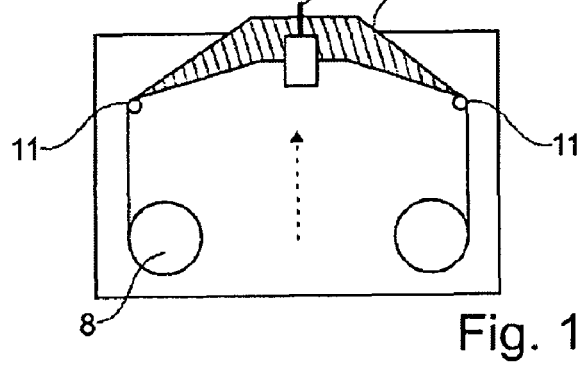 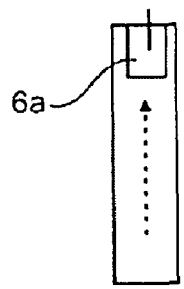
Fig. 13  Fig. 14
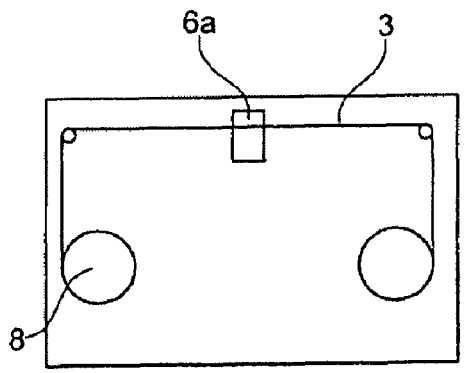 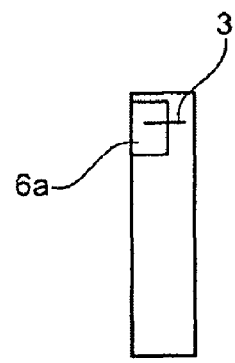
Fig. 15  Fig. 16
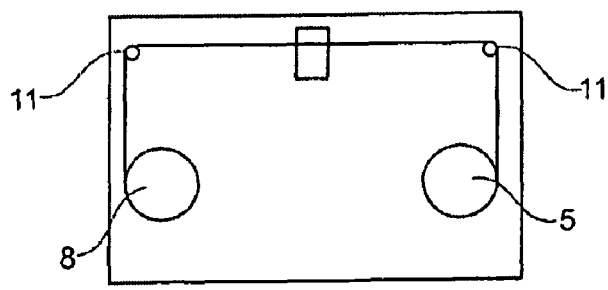 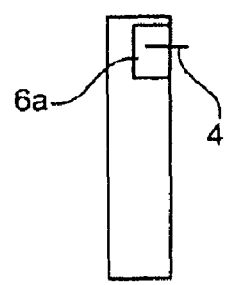
Fig. 17  Fig. 18

LANCING SYSTEM

CROSS REFERENCE TO RELATED APPLICATION

This application is a continuation-in-part of International Application No. PCT/EP2008/006797, filed Aug. 19, 2008, which claims the benefit of European Patent Application No. EP 07 016 808.3, filed Aug. 28, 2007, the entire disclosures of which are hereby incorporated by reference.

BACKGROUND

The present invention relates to a lancing system having a lancet carrier tape that supports a plurality of lancets, a transport means serving to move the lancet carrier tape in a feed or transport direction along a transport path and to thereby move lancets of the lancet carrier tape one after the other to a puncturing position, and a lancing drive for causing a lancet that occupies a puncturing position to perform a puncturing movement. A lancing system of that kind has been known, for example, from DE 28 03 345 B1.

In the case of the known lancing system the lancet carrier tape is arrested for a puncturing operation by pins passed through holes in the tape, and the lancet is then moved relative to the tape in transverse direction to the latter.

A disadvantage of the known lancing system is seen in its complex mechanics which results in rather large dimensions of the lancets and of other system components.

SUMMARY

An object of the invention is therefore to show how a compact and low-cost lancing system having a lancet carrier tape can be provided.

That object is achieved by a lancing system having the features defined in Claim 1. Advantageous further developments of the invention are the subject-matter of the subclaims. Further, the object is also achieved by a lancing system having the features defined in Claim 12.

In a lancing system according to the invention, a lancet having been brought into a puncturing position is moved in the puncturing direction together with the portion of the lancet carrier tape on which the lancet is supported. There is therefore no need for costly measures aimed at arresting the lancet carrier tape and at displacing the lancet relative to the tape. However, the feature of the invention which provides that, for performing a puncturing operation, the lancet is moved in the puncturing direction together with the lancet carrier tape, leads to the problem that the lancet carrier tape must be movable relative to a device case in the puncturing direction. And the lancet carrier tape must not tear during that movement. Especially, it is a requirement that the lancet carrier tape can be moved very quickly together with the puncturing lancet in order to produce the least possible pain.

The invention solves this problem by providing that once a lancet has been moved to the puncturing position at least one element of the transport means, arranged behind the puncturing position in the transport direction, performs a compensating movement before or during the puncturing movement of that lancet.

For example, the transport means may comprise a winding device which initially performs a forward rotary step to bring a lancet to its puncturing position, and then performs a reverse rotary step to unwind the length of tape from the winding device required for a puncturing movement of a lancet that has been moved to the puncturing position.

The forward rotary step pulls a lancet into the puncturing position, i.e. stretches the tape. A subsequent reverse rotary step unwinds the tape from the winding device thereby releasing a sufficient length of the tape for the puncturing movement. In this connection, it is also possible to perform the reverse rotary step prior to initiating the puncturing movement so that the length of the lancet carrier tape between the puncturing position and the winding device will be loose and relaxed. During the puncturing movement, a tape section carrying the lancet in the puncturing position can then be moved relative to the winding device without any problem. The reverse rotary step may be carried out in such a case by a drive of the winding device moving in reverse direction.

There is also the possibility to perform the reverse rotary step during the puncturing movement. This can be achieved, for example, by providing that a driving element, which engages the winding device during the forward rotary step to drive the winding device, is uncoupled from the winding device for the reverse rotary step. The winding device then can rotate freely and can yield to any tension encountered during the puncturing movement by rotating in reverse direction so that the length of tape needed for a puncturing movement will be unwound. The driving element may, for example, consist of a clutch, for example a self-acting clutch such as an overrunning clutch, which while transmitting a torque for forward rotation of the winding device gets uncoupled in the reverse direction so that the winding device can rotate freely in reverse direction. There is, however, also the possibility to use an externally switched clutch, for example a jaw clutch which is disengaged by operation of the lancing drive.

The compensating movement of the at least one part of the transport means, provided for by the invention, may by carried out for example also by a tape guiding element that may be provided in a bend of the transport path and about which the lancet carrier tape may be bent. Moving such a tape-guiding element, being part of the transport means, can reduce the curvature of the tape so as to release the length of the tape required for a puncturing movement. Preferably, the puncturing position is located between two movable tape-guiding elements about which the lancet carrier tape is bent.

Preferably, the at least one tape-guiding element can be moved between a first position in which the lancet carrier tape is bent about the tape-guiding element at a first bending angle, and a second position in which the lancet carrier tape is bent to a lesser degree or not at all, and is moved toward a second position once a lancet has been located in the puncturing position.

The mobility of the tape-guiding element, provided for by the invention, can be achieved for example by making the element slidable. The tape-guiding element can then yield to increased tension of the tape, resulting from a puncturing movement, by performing a displacing movement against the action of a spring.

The compensating movement of at least one part of the transport means, provided for by the invention, may also consist in a pivoting movement, which may be performed, for example during a puncturing movement, by two pivot arms that enclose between them the puncturing position and each of which comprises a tape-guiding element which is arranged in a bend of the transport path and about which the lancet carrier tape is bent.

The two pivot arms and their tape-guiding elements may, for example, guide the tape along a U-shaped toothed rod that may be pivoted during the puncturing operation about a geometric axis oriented at a right angle to the puncturing direction. The tape section that carries the puncturing lancet may likewise carry out the puncturing movement as a pivoting movement or as a linear movement.

The lancets are oriented on the lancet carrier tape preferably transversely to the latter's longitudinal direction. Between the lancets, test fields may be provided on the lancet carrier tape for analyzing a sample of a body liquid collected by the puncturing operation. In that case, the test field can then be moved into the puncturing position for taking up a sample of a body liquid, and the lancing drive may be used to carry out a puncturing movement by which the test field is moved to a puncture wound that has been produced before by a puncturing operation.

Preferably, the movement of the lancet carrier tape by the lancing drive during a puncturing operation is such that the lancet carrier tape remains connected with the puncturing lancet. During a puncturing movement, the lancet carrier tape is bent by a bending means acting on its forward longitudinal edge, viewed in the puncturing direction, so that the tip of the lancet will be lifted off the lancet carrier tape. The rear portion—in the puncturing direction—of the lancet, opposite the lancet tip, remains however connected with the lancet carrier tape throughout the full puncturing movement.

The transport means preferably comprises a winding device that winds up the lancet carrier tape in steps to successively bring lancets into the lancing position. The puncturing movement may be effected in parallel to the geometric axis about which the winding device can be rotated, or at a right angle to that direction.

However, the mobility of the lancet carrier tape required for a puncturing movement can also be obtained without a reverse rotary step by using a lancet carrier tape, as provided for in Claim 12, that will be elongated elastically by each puncturing movement. Each puncturing movement effects a change in the length of the part of the lancet carrier tape that is enclosed between the puncturing position and the winding-up means. That change in length may be effected, as described in the preceding paragraph, by unwinding the lancet carrier tape from the winding device, or by elastic elongation of the lancet carrier tape.

BRIEF DESCRIPTION OF THE DRAWINGS

Further details and advantages of the invention will be described hereafter with reference to certain embodiments and to the attached drawings. The features described may be made the subject of claims either individually or in any combination. Identical and corresponding components are indicated in the attached Figures by the same reference numerals. In the drawings:

FIG. 5 shows a diagrammatic representation of another embodiment of a lancing system, before a puncturing movement is carried out;

FIG. 6 shows a side view corresponding to FIG. 5;

FIG. 7 shows the embodiment illustrated in FIG. 5, performing a puncturing movement;

FIG. 8 shows a side view corresponding to FIG. 7;

FIG. 11 shows a diagrammatic representation of another embodiment of a lancing system, before a puncturing movement is carried out;

FIG. 12 shows a side view corresponding to FIG. 11;

FIG. 13 shows the embodiment illustrated in FIG. 11, performing a puncturing movement;

FIG. 14 shows a side view corresponding to FIG. 13;

FIG. 15 shows a diagrammatic representation of another embodiment of a lancing system, before a puncturing movement is carried out;

FIG. 16 shows a side view corresponding to FIG. 15;

FIG. 17 shows the embodiment illustrated in FIG. 15, performing a puncturing movement;

FIG. 18 shows a side view corresponding to FIG. 17;

DESCRIPTION OF THE SELECTED EMBODIMENTS

Figure 1:
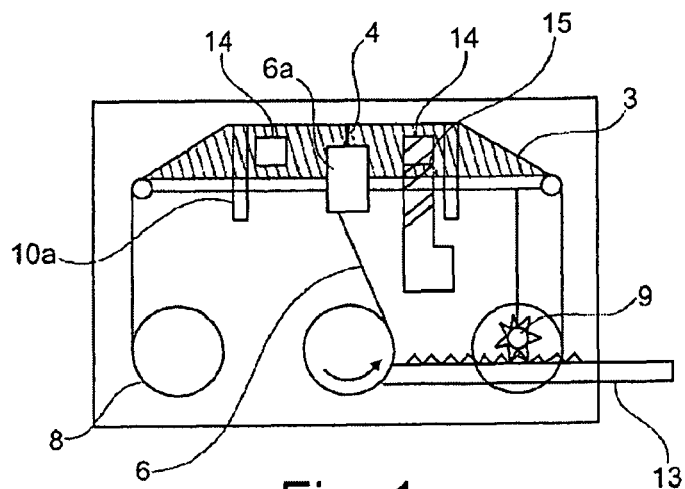
FIG. 1 shows a diagrammatic representation of one embodiment before a puncturing movement is carried out.

FIG. 1 shows a diagrammatic representation of one embodiment of a lancing system 1 with the housing 2 in open condition. The lancing system 1 comprises a lancet carrier tape 3, carrying a plurality of lancets 4 arranged transversely to the lengthwise direction of the tape 3. A winding device 5, configured as a driven roller in the illustrated embodiment, serves to wind up and thereby move the lancet carrier tape 3 in its longitudinal direction so that the lancets 4 of the lancet carrier tape 3 successively come to occupy a puncturing position in which the lancets, together with the tape section on which they are carried, can be accelerated for a puncturing movement by a lancing drive 6 in order to puncture a part of a body 7—illustrated in FIG. 2, that shows a side view corresponding to FIG. 1—applied against an opening 16 of the housing.

In the illustrated embodiment, the lancet carrier tape 3 is wound up on a supply roller 8, similar to a tape of a sound recorder, and can be unwound from that roller and wound up in steps on the driven roller of the winding device 5. The lancet carrier tape 3 may be exchangeably arranged in a housing 2 of a lancing system, for example as part of a cassette, or may be firmly installed in a device that has to be discarded once all lancets 4 of the lancet carrier tape 3 have been used up. Instead of using a supply roller 8 it is, for example, also possible to use a stack formed by a fanfolded lancet carrier tape 3.

During the transport movement, prior to reaching the puncturing position, the lancet carrier tape 3 with a lancet 4 runs past deflection means 10a that causes the lancet carrier tape 3 to be deflected by 90°. After use of a lancet 4, the respective section of the lancet carrier tape 3 is moved past a second deflection means 10b by which the lancet carrier tape is returned to its original orientation. The lancet carrier tape 3 is guided on this way by guide elements 11 which enclose between them the puncturing position. The guide elements 11 are preferably configured as pins. There is, however, also the possibility to use rollers in order to allow the tape to be transported with the least possible friction.

In the described embodiment the winding device 5, the guide elements 11 and the deflection means 10a, 10b form together the transport means by which the lancet carrier tape 3 is moved along a transport path in a transport direction in order to successively move lancets 4 of the lancet carrier tape 3 to the puncturing position.

Figure 2:
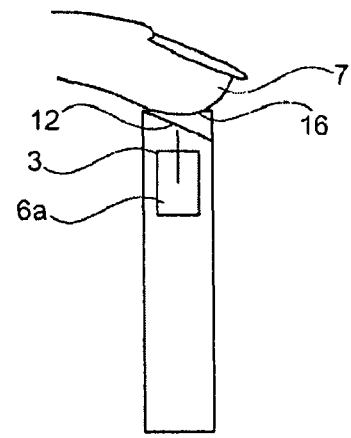
FIG. 2 shows a side view corresponding to FIG. 1.

FIG. 2 shows a diagrammatic side view corresponding to FIG. 1, showing a part of a body 7 applied against the housing's opening 16, namely a finger in which a puncture wound is to be produced for collection of a sample of a body liquid.

The lancet carrier tape 3 is moved in the longitudinal direction by a forward rotary step of the winding device 5 until one lancet 4 occupies the puncturing position illustrated in FIG. 1. For example, the lancet 4 may form an elevation on the lancet carrier tape 3 that comes to abut against a stop of the coupling head 6a of the lancing drive 6 when the lancet 4 has reached the puncturing position. The coupling head 6a may, for example, consist of two clamping surfaces that can be moved toward each other and which form between them in their open position a gap through which the lancet carrier tape 3 is guided, in which case a lancet 4 will come to abut against a bottleneck of the gap 4 in the puncturing position. During a puncturing operation the two clamping surfaces of the coupling head are pressed together in order to securely hold the lancet 4 and the lancet carrier tape 3. Following the puncturing operation, the clamping surfaces are moved apart so that the gap will open far enough to let the lancet 4 just used pass the gap.

The winding device 5 is driven via a driving element 9 that engages the winding device 5 when the winding roller turns in forward direction, which is the case during positioning of the lancet 4 in the puncturing position. In the illustrated embodiment, the driving element 9 is a toothed wheel that transmits a torque for rotation of the winding device 5 in forward direction, while it is uncoupled from the winding device 5 for a puncturing movement to allow the winding device 5 to freely rotate in reverse direction, In FIG. 1 the drive element 9 is shown in the position in which it is coupled with the winding device 5 while in FIG. 3 it is shown in its uncoupled position. The drive element 9 is coupled with the drive head 6a via a rod in the illustrated embodiment, and is moved in the lancing direction when a puncturing movement is performed. In its coupled position the drive element 9, configured as a toothed wheel or more precisely as a toothed roller, is supported on a toothed rod 13 and on a driving gear 14 of the winding device 5 illustrated in FIG. 3. The driving gear 14 of the winding device 5 is positioned beside the toothed rod 13 so that the drive element is coupled with both the toothed rod 13 and the driving gear 14.

For operating the winding device to position a lancet 4 in the puncturing position, the toothed rod 13, which projects from the housing 2, is pushed inwards by the user. The movement of the toothed rod 13 is transmitted to the winding device via the drive element 9 and the driving gear of the winding device 5—not shown—so that the winding device performs a rotary movement. When a puncturing operation is carried out, the drive element 9 and the coupling head 6a are moved together in the lancing direction, and are lifted off the toothed rod and the driving gear of the driving means, being thereby uncoupled from the winding device 5 and allowed to rotate freely.

During a puncturing movement the drive element, which is coupled with the winding device 5 for forward rotation, is uncoupled from the winding device 5 so that the winding device 5 is allowed to rotate freely in reverse direction. Consequently, the lancet carrier tape 3 can unwind from the supply roller 8 and from the winding device 5 during a puncturing movement and is thus given sufficient mobility for the lifting movement performed during the puncturing movement.

The toothed rod 13 additionally serves for tensioning a drive spring—not shown—of the lancing drive 6. To this end, there is provided a drive element—not shown—of the lancing drive 6 that engages the teeth of the toothed rod 13.

The winding device 5 engages the drive element 9 via a slip coupling. This guarantees that the toothed rod can be pushed into the case 2 of the device always over the same length. Once a lancet 4 has reached the puncturing position, the lancet carrier tape 3 gets blocked and the winding device 5 will be uncoupled from the further movement of the toothed rod 13 by the slip clutch.

Figure 3:
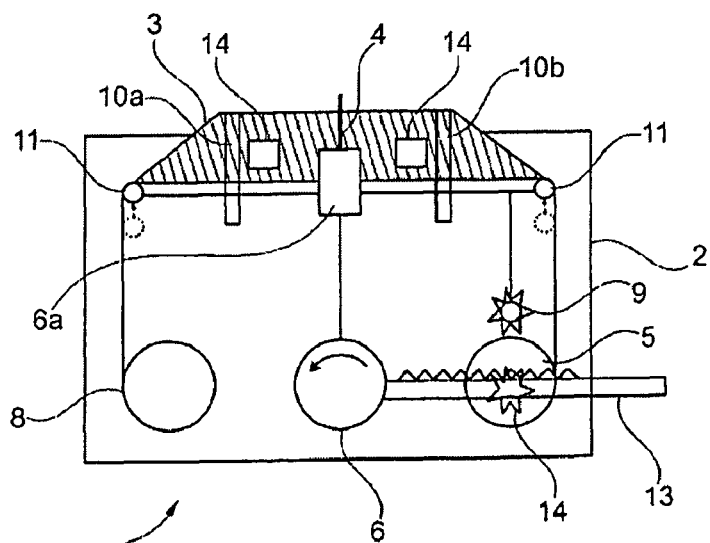
FIG. 3 shows the embodiment illustrated in FIG. 1, performing a puncturing movement.
Figure 4:
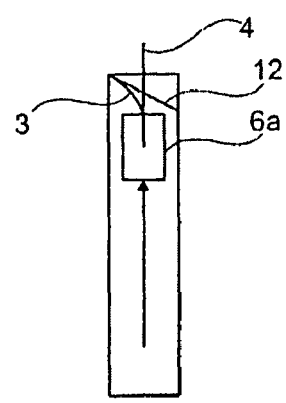
FIG. 4 shows a side view corresponding to FIG. 3.

FIG. 3 shows the embodiment illustrated in FIG. 3 during a puncturing movement, i.e. at the reversal point of the movement at maximum travel of the lancing drive, while FIG. 4 shows a corresponding side view.

In the illustrated embodiment the two guide elements 11 are likewise moved in the lancing direction during a puncturing operation. That feature provides the advantage to improve the mobility of the tape 3 so that puncturing to collect a sample of a body liquid can be carried out as quickly as possible and, thus, with little pain.

During the puncturing movement the forward longitudinal edge of the tape 3, viewed in the puncturing direction, is bent over so that the tip of the puncturing lancet 4 is lifted off the tape 3 to puncture a part of a body 7 applied against the device opening 9 without being obstructed by the tape 3. Bending over the longitudinal edge of the tape 3 may be effected, for example, by an inclined surface 12, for example a web, arranged laterally of the puncturing position so that the edge of the tape will abut against, and be deflected by, the inclined surface for performing the puncturing movement. A suitable bending-over means with an inclined surface 12 is illustrated in FIGS. 2 and 4. In FIGS. 1 and 3, the bending-over means is not shown for the sake of clarity.

Between the lancet 4, the lancet carrier tape 3 carries test fields 14 intended to analyze the sample of the body liquid that has been collected by a puncturing operation. Following the puncturing operation, the winding device 5 performs a further forward rotary step to move a test field 14 to the puncturing position. The coupling head 6a of the lancing drive 6 then performs another puncturing movement by which the test field 14 is moved to a puncture wound, produced by the preceding lancing operation in the part of the body 7 that is applied against the case opening 9, for absorbing a sample of a body liquid. During that puncturing movement, just as during the puncturing movement performed using a lancet 4, the winding device 5 again performs a reverse rotary step in order to provide the required mobility for the tape.

Once a sample has been taken up by the test field 14, the winding device 5 performs another forward rotary step to move the test field 14, with the sample of the body liquid taken up, to an analyzing position in which the sample of the body liquid is analyzed by a measuring means 15 of the lancing system. The test field 14 may, for example, contain indicator reagents that react with an analyte contained in the sample of the body liquid to produce a change in color. The change in color may be interpreted photometrically to determine the analyte concentration, for example the glucose concentration. The measuring means 15 may be designed as a photometric measuring system in which an evaluation unit may be integrated for determination of the concentration of the component. Test results may be indicated by an indicator means, for example a liquid crystal display, arranged on the outside of the case 2.

FIGS. 5 to 8 show a diagrammatic representation of another embodiment of a lancing system that differs from the embodiment described before in that puncturing is performed in a direction parallel to a geometric axis of rotation for the rotary movement of the winding device 5. In the case of that embodiment, the part of the body 7, in which the puncture wound is to be produced, is applied against a device opening 16 provided on the upside of the case 2, while a corresponding device opening 9 of the embodiments illustrated in FIGS. 1 to 4 is located on a narrow side of the case. Consequently, the embodiment illustrated in FIGS. 5 to 8 works without a deflection means to rotate the lancet carrier tape 3 which leads to corresponding simplification of the tape guiding arrangement.

For the rest, that embodiment could be designed in the same manner as the one described before, especially insofar as the winding device 5 might provide the required mobility for the tape during the puncturing movement by a reverse rotary step.

However, in the embodiment illustrated in FIGS. 5 to 8, the necessary mobility for the puncturing movement is provided by a movement of the guide elements 11. In FIG. 5, the guide elements 11 are shown in a first position in which the lancet supply tape 3 is bent about the guide elements 11 at a bending angle of 70° to 110°, preferably 90°. That first position is occupied by the guide elements 11 when the lancet carrier tape 3 is moved in the transport direction in order to move a new lancet 4 to the puncturing position.

In FIG. 7, the guide elements 11 are shown in a second position in which the lancet carrier tape 3 is bent about the guide elements 11 at a smaller bending angle. To illustrate that difference more clearly, the guide elements 11 are also shown in that second position in FIG. 7. At the moment of a lancing action, the guide elements 11 are in that second position.

The guide elements 11 are mounted in displaceable fashion so that they can be moved between the first and the second positions. There is, for example, the possibility to couple the guide elements 11 with a spring that produces a restoring force when being displaced from the first position toward the second position. An increase in tension of the tape, caused especially by a puncturing movement, causes the guide elements 11 to move toward the second position. The first and the second positions may be extremal positions that are reached never or only on rare occasions as a low degree of tension may exist also during the tape feed, which already may produce a slight deflection of the tape from the first position.

There is further the possibility to move the guide elements 11 actively between the first and the second positions to provide the necessary mobility of the tape for the puncturing movement. For example, the guide elements 11 may be moved by a drive from the first to the second position after a lancet 4 has reached the puncturing position, but before a puncturing operation is initiated.

Movable tape guiding elements 11 of the kind described before may be used also in a tape guiding arrangement according to the embodiments of FIGS. 1 to 4, instead of the reversible winding device.

One advantage of the movable tape guiding means 11 is seen in the fact that the winding device 5 can be provided with a reversing block. Also it is then easier to couple a toothed rod 13, as shown in FIGS. 1 and 3, with the winding device 5 via a slip clutch.

In the embodiments illustrated in FIGS. 5 to 8 there may be additionally provided, in an effort to minimize friction moments, that the guide elements 11 can move also in the puncturing direction. This can be achieved in a favorable way by designing the guide elements 11 as sleeves that are mounted for displacement in the puncturing direction, for example on bearing pins on which they are permitted to rotate during transport of the tape.

For greater clarity of the illustration the details of the lancing drive 6 and the drive of the winding device 5 are not shown in FIGS. 5 to 8. In principle, these details may be configured in the same way as in the preceding embodiment.

Figure 9:
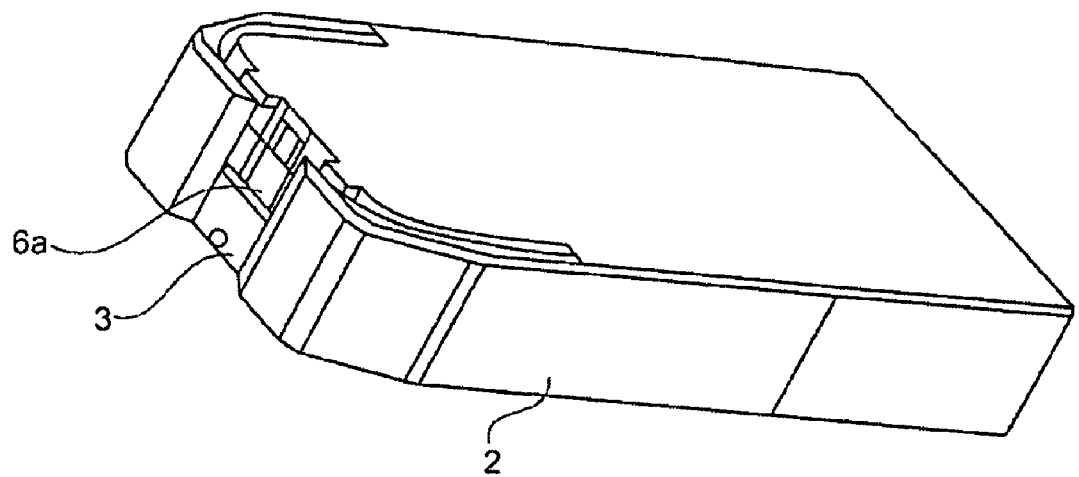
FIG. 9 shows a diagrammatic representation of another embodiment of a lancing system, before a puncturing movement is carried out.
Figure 10:
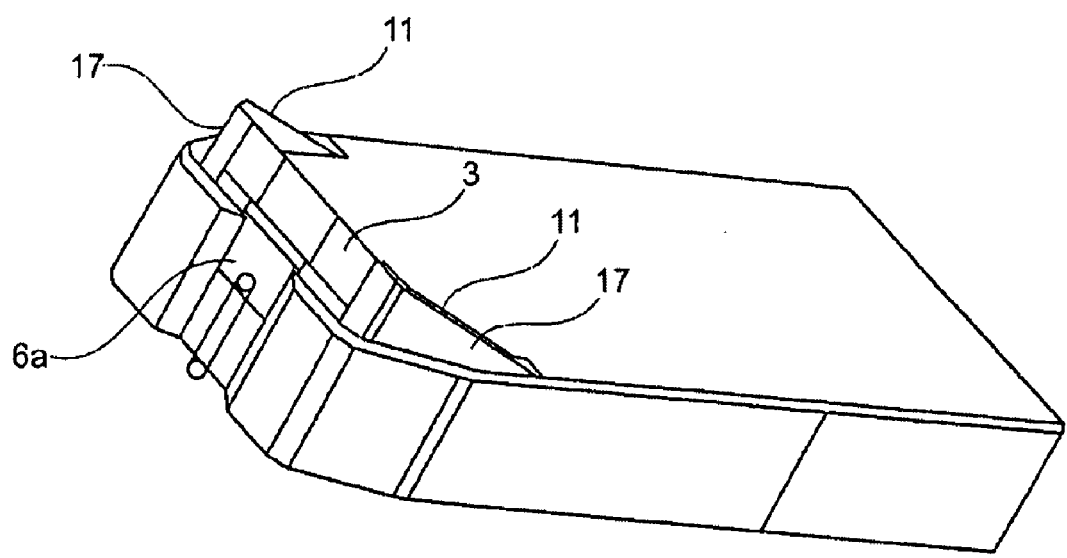
FIG. 10 shows the embodiment illustrated in FIG. 9, performing a puncturing movement.

FIGS. 9 and 10 show a further embodiment of a lancing system where the puncturing direction is parallel to the geometric axis about which the winding device 5 rotates for winding up the lancet carrier tape 3, similar to the embodiments of FIGS. 5 to 8. The transport means comprises two pivot arms 17 which enclose between them the puncturing position and each of which carries a tape-guiding element 11 which is located in a bend of the transport path and about which the lancet carrier tape 3 is bent. During a puncturing movement, the pivot arms 17 perform a pivoting movement thereby moving from the position illustrated in FIG. 9 to the position illustrated in FIG. 10.

The tape-guiding elements 17 may have the same configuration in that embodiment as in the embodiments described before. There is, for example, also the possibility to configure the tape-guiding elements as curved guide surfaces that support the lancet carrier tape 3 and that extend in the transport direction.

The two pivot arms 17 may be connected at their ends and may thus form sort of a horseshoe link. Preferably, however, the pivot arms 17 are not in contact one with the other. In the illustrated embodiment, the puncturing position and the coupling head 6a are located between the pivot arms 17. The coupling head 6a that grips a lancet 4 in the puncturing position together with the tape section on which it is carried performs, however, the same linear movement as in the embodiments described before.

The pivoting movement of the pivot arms 17 occurs about a geometric axis that extends perpendicularly to the puncturing direction.

The embodiment illustrated in FIGS. 9 and 10 is a tape cassette containing the lancet carrier tape 3 and the coupling head 6a of the lancing drive 6. That tape cassette is intended to be inserted into a matching compartment of a lancing device whereby the lancing drive 6 of the lancing device will be coupled with the coupling head 6a of the illustrated tape cassette. The lancing device 6 further comprises a drive, for coupling the device with the winding device 5 of an inserted tape cassette, further a bending means for bending the longitudinal edge of the tape, and the like.

The illustrated tape cassette and a matching lancing device form together the lancing system. A lancing device can be reused again and again provided a tape cassette in which all lancets on the lancet carrier tape 3 have been used is exchanged against a fresh tape cassette.

FIGS. 11 to 14 show a diagrammatic representation of a further embodiment of a lancing system where the tape guide provides for deflection of the lancet carrier tape 3 by 90°, similar to the embodiments of FIGS. 1 to 4. The winding device 5 of the embodiment illustrated in FIGS. 11 to 14 is coupled with a reversing block, for example a ratchet mechanism, so that the winding device 5 can rotate in forward direction only. The mobility of the tape required for the puncturing movement is provided by the elastic behavior of the lancet carrier tape 3. At the moment of the puncturing movement, the lancet carrier tape 3 is extended elastically thereby providing the required elongation of that portion of the lancet carrier tape 3 that extends between the puncturing lancet 4 and the winding device 5.

FIGS. 15 to 18 show another embodiment of a lancing system where the tape guide corresponds to the embodiment illustrated in FIGS. 5 to 8. At the moment of a puncturing movement the lancet 4 is moved in parallel to the geometric axis of rotation about which the winding device 5 rotates. In this case as well reverse rotation of the winding device is prevented by a reversing block, and the required mobility of the lancet carrier tape 3 is achieved by elastic elongation.

Figure 19:
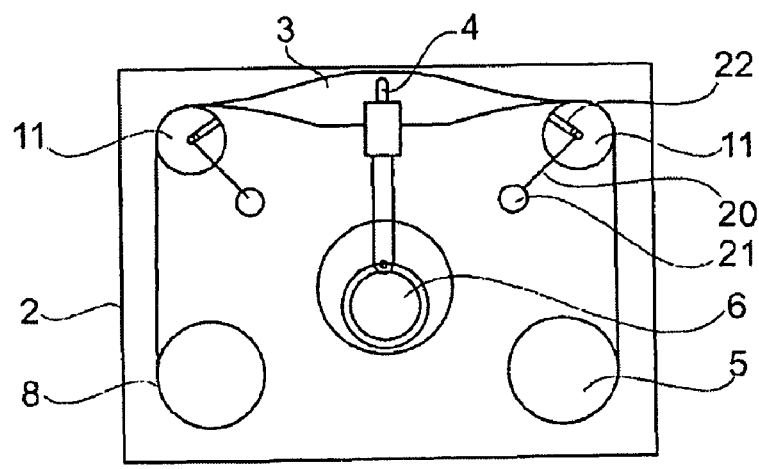
FIG. 19 shows a diagrammatic representation of another embodiment of a lancing system, before a puncturing movement is carried out.
Figure 20:
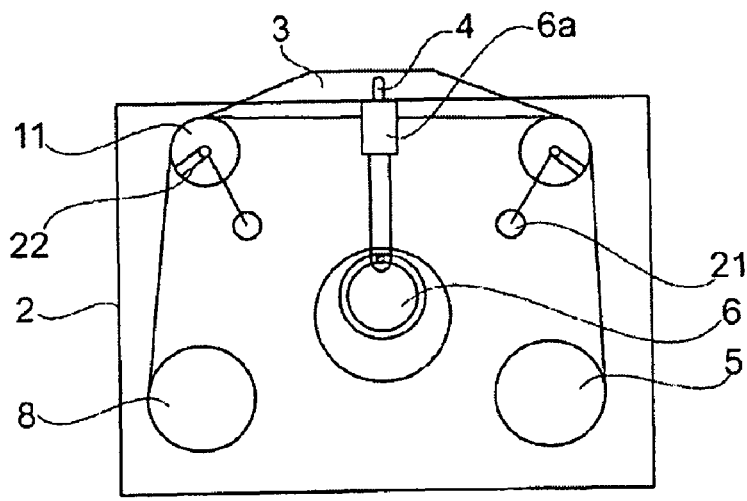
FIG. 20 shows the embodiment illustrated in FIG. 19, performing a puncturing movement.

FIGS. 19 and 20 show another embodiment of a lancing system, before a puncturing movement is carried out (FIG. 19) and during a puncture (FIG. 20). This embodiment differs from the embodiment shown in FIG. 7 mainly in that the guiding means 11 are moveable between first and second positions along an arc instead of a linear movement as indicated in FIG. 7. The guide elements 11 are mounted on flat springs 20. The flat springs 20 are each fixed to a fixed bearing 21 and a guide element 11. Hence, the guide elements 11 can move along a section of a circular arc. The centre of that circular arc is defined by the fixed bearings 21. The movement of the guide elements 11 along such an arc is supported by a rail or other guide means 22.

A puncturing movement of a lancet 4 causes tensioning of the carrier tape 3 and thereby a pivoting movement of the guide elements 11 as shown in FIG. 20. This pivoting movement releases tension in the tape 3 and thereby accommodates a puncture.

The strength of the springs 20 should be high enough to prevent such a pivoting movement of the guide elements 11 during a transport movement of the tape 3 caused by the winding device 5. However, the springs 20 should be weak enough to facilitate pivoting movement of the guide elements 11 during a puncture.

Figure 21:
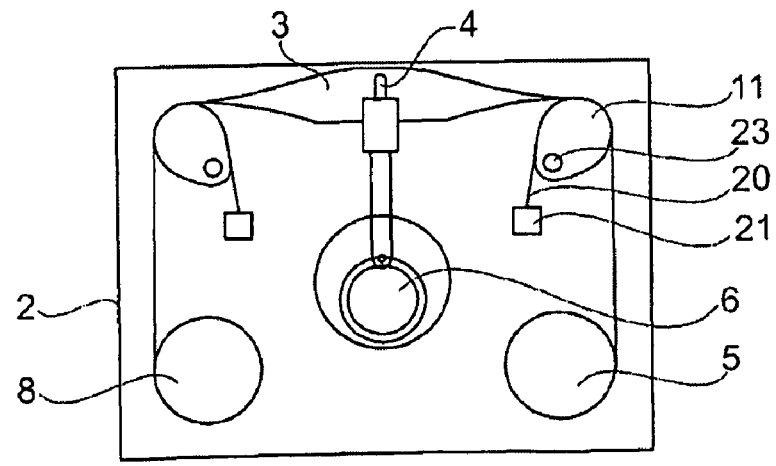
FIG. 21 shows a diagrammatic representation of another embodiment of a lancing system, before a puncturing movement is carried out.
Figure 22:
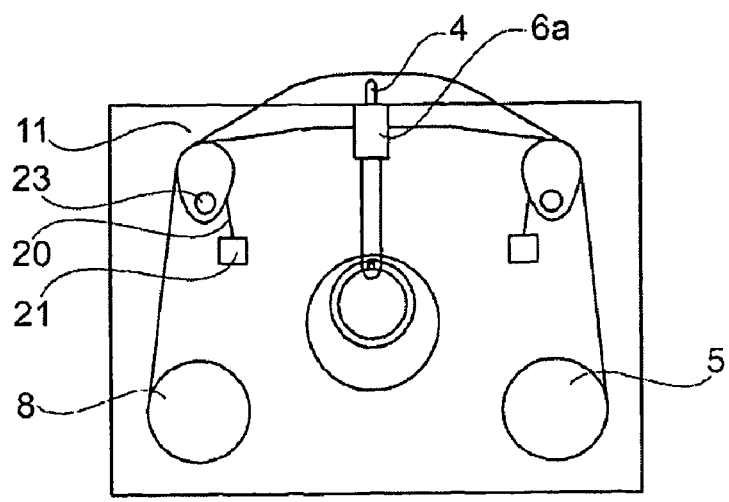
FIG. 22 shows the embodiment illustrated in FIG. 21, performing a puncturing movement.

FIGS. 21 and 22 show another embodiment which differs from the previous embodiment in that the guide elements 11 can rotate about an axis 23 which is arranged eccentrically in the guide elements 11. The guide elements 11 are connected by flat springs 20 to fixed bearings 21. Like in the previous embodiment of FIGS. 19 and 20, the flat springs 20 provide a restoring force which moves the guide elements 11 after a puncture back into their original position.

Figure 23:
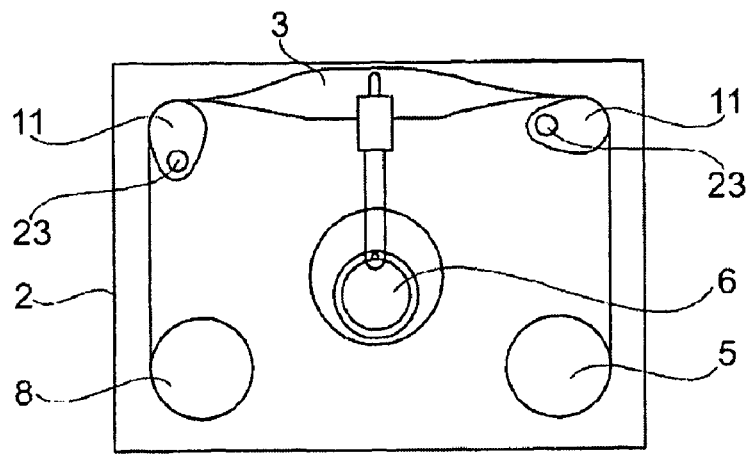
FIG. 23 shows a diagrammatic representation of another embodiment of a lancing system, before a puncturing movement is carried out.
Figure 24:
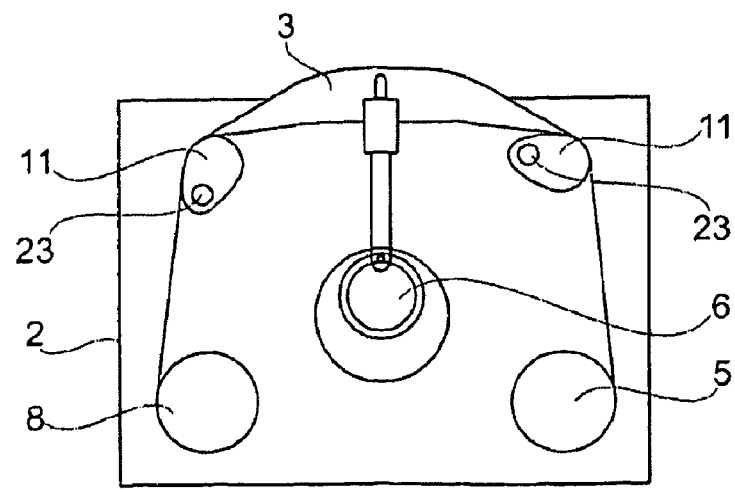
FIG. 24 shows the embodiment illustrated in FIG. 23, performing a puncturing movement.
Figure 25:
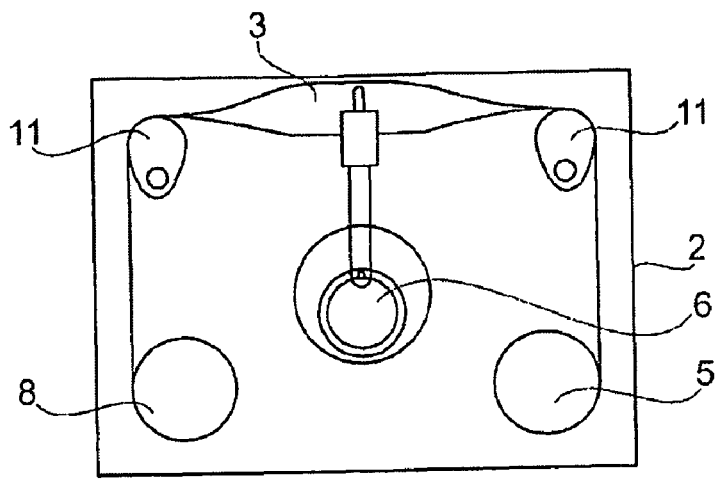
FIG. 25 shows a diagrammatic representation of another embodiment of a lancing system, before a puncturing movement is carried out.
Figure 26:
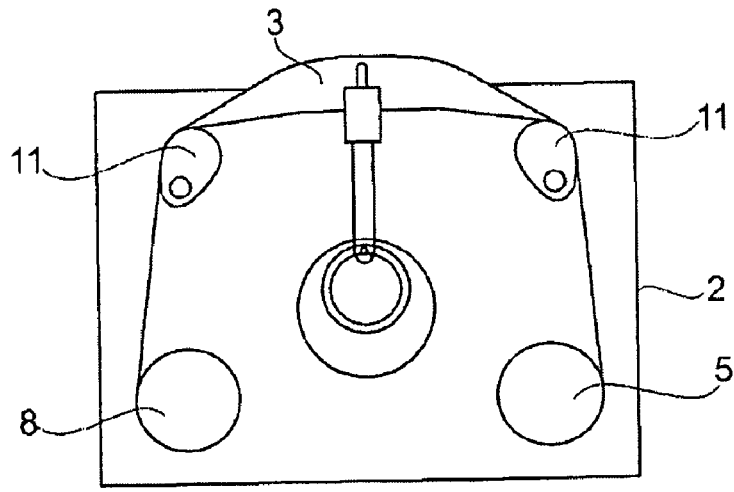
FIG. 26 shows the embodiment illustrated in FIG. 25, performing a puncturing movement.

FIGS. 23 and 24 show schematically another embodiment. This embodiment differs from the embodiment shown in FIGS. 21 and 22, like the embodiment shown schematically in FIGS. 25 and 26, only with respect to the fixed bearings 21 and the springs 20. In the embodiments shown in FIGS. 23 to 26 the fixed bearings are located inside the guide elements 11. Springs to provide a restoring force are not shown in these embodiments, but may be arranged inside the guide elements 11.

Figure 27:
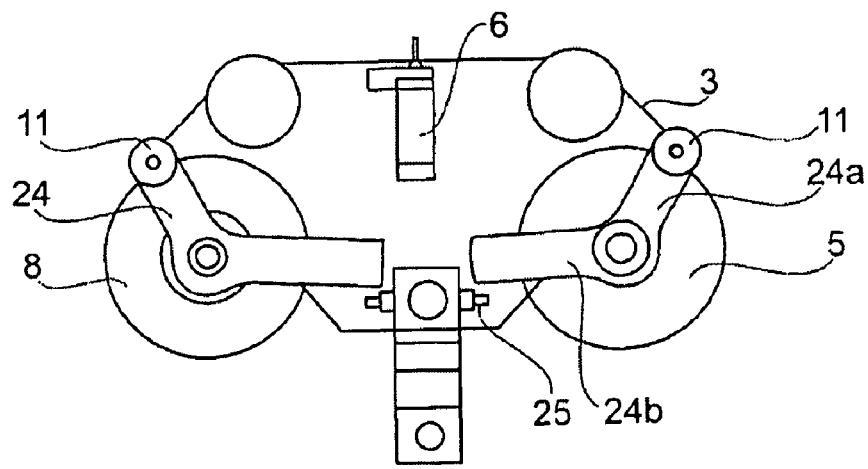
FIG. 27 shows a diagrammatic representation of another embodiment of a lancing system, after a puncturing movement is carried out.

FIGS. 27 to 30 show schematically another embodiment of a lancing system. FIG. 27 shows the system after a lancing has been performed but before a fresh lancet has been moved into the puncturing position. When the winding device 5 is actuated to wind up the lancet carrier tape 3 and thereby to move a fresh lancet into the puncturing position, the tape is tensioned and the guide elements 11 move to relieve that tension. In the embodiment shown in FIGS. 27 to 30 the moveable guide elements 11 are arranged on pivoting arms 24 comprising sections 24a and 24b. Movement of these arms 24 is restricted by a moveable block 25, for example an abutment. The movable block 25 forms a locking member which is movable between an active position in which it restricts the compensating movement and an inactive position in which it does not.

The arms 24 pivot about the same axis as the supply roller 8 or the winding device 5, respectively. The sections 24a and 24b of the arms 24 are arranged at an angle with respect to each other. The angle may be between 110° and 140°, especially between 120° and 130°, for example.

Figure 28:
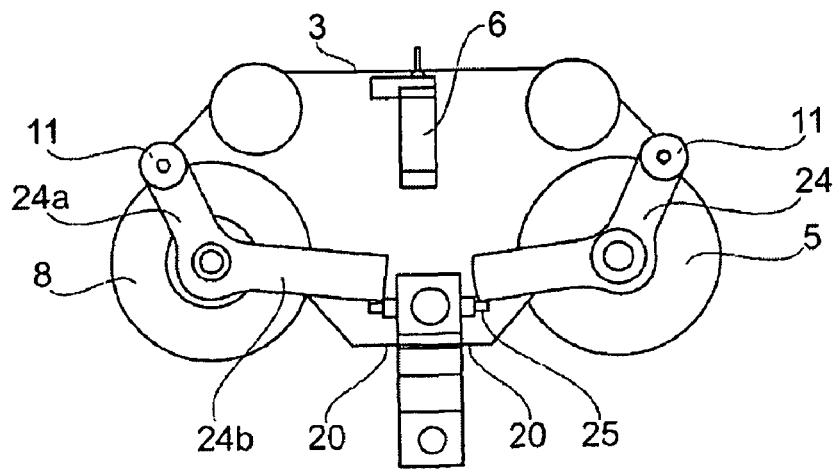
FIG. 28 shows the embodiment illustrated in FIG. 27, while the carrier tape is being wound up to transport a fresh lancet into the puncturing position.
Figure 29:
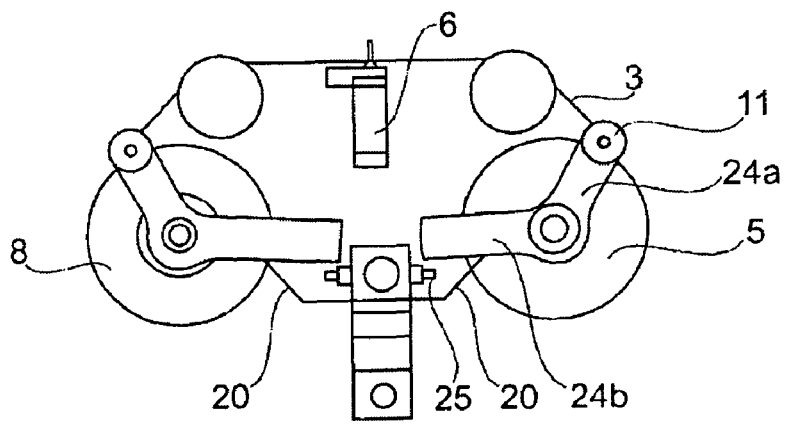
FIG. 29 shows the embodiment illustrated in FIG. 27, before a puncturing is carried out but after a fresh lancet has reached the puncturing position.

A pivoting movement of the arms 24 during movement of a fresh lancet into the puncturing position, i.e. when the carrier tape 3 is being wound up, causes sections 24b to abut against the abutment 25 as shown in FIG. 28. After a fresh lancet has reached the puncturing position the arms 24 return to their original position as shown in FIG. 29. This can be achieved by means of springs, for example by means of flat springs 20. The springs 20 cause continually a tension of the tape. Therefore, the movable block 25 should not arrest the arms 24 and the guide elements 11 completely, i.e. prevent movement completely, when it is in its active position. Rather the movable block 25 should in its active position only prevent large compensating movements that are necessary to accommodate a puncturing motion, but allow minor movements necessary to maintain a tension of the tape.

Figure 30:
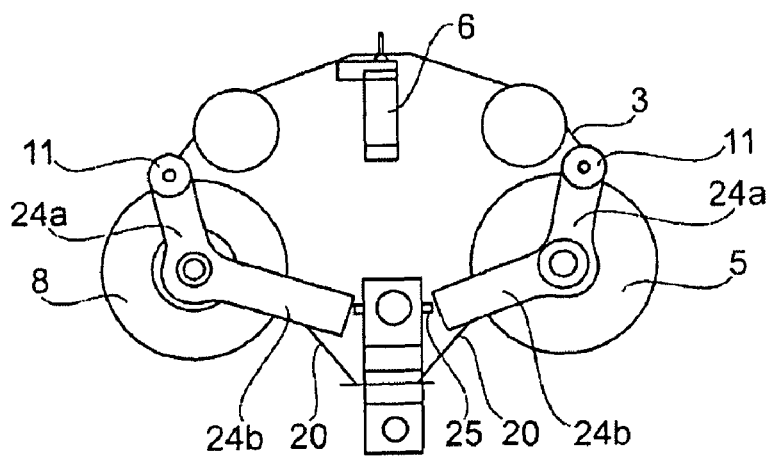
FIG. 30 shows the embodiment illustrated in FIG. 27, performing a puncturing movement.

After a fresh lancet has reached the puncturing position, the abutment 25 is retracted to prepare the system for a puncture. During a puncture the arms 24 can therefore pivot freely as shown in FIG. 30. As a consequence the guide elements 11 can move much further during a puncture than during transport of a fresh lancet into the lancing position. Hence, the arms 24 can accommodate a puncture movement of the tape 3. FIG. 28 shows the abutment 25 in its active position restricting movement of the arms 24. FIG. 30 shows the abutment 25 in its inactive position in which the abutment 25 does not restrict movement of the arms 24.

LIST OF REFERENCE NUMERALS

1 Lancing system
2 Housing
3 Lancet carrier tape
4 Lancet
5 Winding device
6 Lancing drive
6a Coupling head of the lancing drive
7 Part of a body
8 Supply roller
9 Drive element
10a, 10b Deflection means
11 Guide element
12 Inclined surface of the bending means
13 Toothed rod
14 Test field 15 Measuring means
16 Case opening
17 Pivot arm
20 Flat spring
21 Fixed bearing
22 Guide means
23 Axis
24 Arm
24a Arm section
24b Arm section
25 locking member

The invention claimed is:

1. Lancing system having
a lancet carrier tape that supports a plurality of lancets arranged transversely to its longitudinal direction;
a transport means serving to move the lancet carrier tape in a transport along a transport path and to thereby move lancets of the lancet carrier tape one after the other to a puncturing position; and
a lancing drive for causing a lancet that occupies a puncturing position to perform a puncturing movement, wherein
during a puncturing movement the lancing drive moves a lancet, that has been brought to a puncturing position, in the puncturing direction together with a portion of the lancet carrier tape on which that lancet is supported and that
once a lancet has been moved to the puncturing position at least one element of the transport means, arranged behind the puncturing position in the transport direction, performs a compensating movement before or during the puncturing movement of that lancet; and
wherein the lancet remains fixed to the portion of the lancet carrier tape during the puncturing movement, wherein the compensating movement allows the lancet and the portion of the lancet carrier tape to move together during the puncturing movement.

2. The lancing system as defined in claim 1, wherein the transport means comprises a winding device that successively brings lancets to the puncturing position by winding up the lancet carrier tape by steps.

3. The lancing system as defined in claim 2, wherein the movement of the at least one part of the transport means is a reverse rotary step of the winding device, and that the winding device performs a forward rotary step to move a lancet to the puncturing position, and then performs the reverse rotary step to unwind a length of tape from the winding device for a puncturing movement of the lancet that has been moved to the puncturing position.

4. The lancing system as defined in claim 1, wherein the reverse rotary step is effected during the puncturing movement.

5. The lancing system as defined in claim 1, wherein a driving element, which en-gages the winding device during the forward rotary step to drive the winding de-vice, and is uncoupled from the winding device for the reverse rotary step.

6. The lancing system as defined in claim 1, wherein the transport means comprises at least one guide element, arranged behind the puncturing position in the transport direction, which is located in a bend of the transport path and about which the lancet carrier tape is bent.

7. The lancing system as defined in claim 6, wherein the guide element can be moved between a first position in which the lancet carrier tape is bent about the guide element at a first bending angle, and a second position in which the lancet carrier tape is bent to a lesser degree or not at all, the guide element being moved toward the second position once a lance has been located in the puncturing position.

8. The lancing system as defined in claim 6, wherein two tape-guiding elements which enclose the puncturing position between them.

9. The lancing system as defined in claim 1, wherein the transport means comprises two pivot arms that enclose between them the puncturing position and each of which comprises a tape-guiding element which is arranged in a bend of the transport path and about which the lancet carrier tape is bent, the pivot arms performing a pivoting movement during a puncturing movement.

10. The lancing system as defined in claim 9, wherein the pivoting movement is effected about a geometric axis oriented at a right angle to the puncturing direction.

11. The lancing system as defined in claim 1, wherein test fields are provided on the lancet carrier tape between the lancets for analyzing a sample of a body liquid collected by the puncturing operation.

12. The lancing system as defined in claim 1, wherein the forward longitudinal edge of the lancet carrier tape, viewed in the puncturing direction, is bent over during a puncturing movement.

13. The lancing system as defined in claim 12, wherein the tip of the lancet that has been moved to the puncturing position is lifted off the lancet carrier tape during the puncturing movement.

14. The lancing system as defined in claim 1, wherein the transport means is coupled with a drive element via a slip clutch.

15. The lancing system as defined in claim 1, wherein for coupling the lancing drive with the lancet carrier tape, the lancing drive is provided with a coupling head comprising a gap through which the lancet carrier tape is guided.

16. The lancing system as defined in claim 1, wherein the compensating movement is performed by a guide element arranged on a pivoting arm.

17. The lancing system as defined in claim 16, wherein a locking member is movable between an active position in which it restricts the compensating movement and an inactive position in which it does not.

18. The lancing system as defined in claim 17, wherein the locking member is an abutment which restricts in its active position movement of the pivoting arm.

19. The lancing system of claim 1, wherein said lancing drive further comprises a coupling head for holding the lancet and the lancet carrier tape.

20. A lancing system, comprising:
a lancet carrier tape;
a plurality of lancets attached to the lancet carrier tape;
a lancing drive for causing at least one of the lancets on the lancet carrier tape to perform a puncturing movement, wherein a portion of the lancet carrier tape moves with the lancet during the puncture movement; and
at least one tape guide element guiding the lancet carrier tape, wherein the guide element is rotatable about an axis that is arranged eccentrically relative to the guide element, the guide element being rotatable about the axis to release tension in the lancet carrier tape during the puncturing movement.

21. The lancing system of claim 20, wherein the lancets arranged transversely to a longitudinal direction of the lancet carrier tape.

22. The lancing system of claim 20, further comprising:
a fixed bearing; and a spring connecting the guide element to the fixed bearing, the spring providing a restoring force to move the guide element back to an original position after the puncturing movement.

23. A lancing system, comprising:
a lancet carrier tape extending in a longitudinal direction between two rollers;
a lancet attached to the lancet carrier tape, wherein the lancet extends transversely to the longitudinal direction of the lancet carrier tape;
a lancing drive configured actuate the lancet to form an incision, wherein a portion of the lancet carrier tape to which the lancet is attached moves with the lancet during actuation of the lancet by the lancing drive;
a first guide element guiding the lancet carrier tape between the two rollers;
a second guide element guiding the lancet carrier tape between the two rollers;
wherein at least one of the first and second guide elements is moveable during actuation of the lancet to provide slack for the portion of the lancet carrier tape that moves with the lancet; and
wherein the lancet remains fixed to the portion of the lancet carrier tape during actuation of the lancet.

24. The lancing system of claim 23, wherein the at least one of the first and second guide elements is rotatable about an eccentric axis, the at least one of the first and second guide elements being rotatable about the eccentric axis to release tension in the lancet carrier tape during actuation of the lancet.

25. A method, comprising:
providing a lancet fixed to a lancet carrier tape, wherein the lancet is oriented in a transverse direction relative to a longitudinal direction of the lancet carrier tape;
indexing the lancet to a puncturing position by winding the lancet carrier tape on a winding device;
unwinding a length of the lancet carrier tape from the winding device after said indexing the lancet to the puncturing position;
performing a puncturing movement with the lancet in the transverse direction, wherein the lancet remains fixed to the lancet carrier tape during said performing the puncturing movement; and
wherein said unwinding the length of the lancet carrier taper occurs before or during said performing the puncturing movement so as to compensate for the puncturing movement.

26. The method of claim 25, further comprising:
moving the lancet out of the puncturing position after said performing the puncturing movement by winding the lancet carrier tape on the winding device.

* * * * *